United States Patent [19]

Convers et al.

[11] 4,366,327

[45] Dec. 28, 1982

[54] PROCESS FOR PRODUCING ETHERS BY REACTING OLEFINS WITH ALCOHOLS

[75] Inventors: Alain Convers, Rueil-Malmaison; Bernard Torck, Boulogne sur Seine; Jean-Paul Euzen, Egully; Pierre Amigues, La Muladiere, all of France

[73] Assignee: Institut Francais du Petrole, Rueil-Malmaison, France

[21] Appl. No.: 258,317

[22] Filed: Apr. 28, 1981

[30] Foreign Application Priority Data

Apr. 28, 1980 [FR] France .................................. 80 09727

[51] Int. Cl.$^3$ .............................................. C07C 41/06
[52] U.S. Cl. .................................................... 568/697
[58] Field of Search ......................................... 568/697

[56] References Cited

U.S. PATENT DOCUMENTS 4,267,393  5/1981  Torck et al. ......................... 568/697

*Primary Examiner*—Howard T. Mars
*Attorney, Agent, or Firm*—Millen & White

[57] ABSTRACT

Process for producing ethers by reacting a catalytic cracking C$_4$ olefinic cut which may contain such impurities as NaOH, an alkanolamine, an alkaline earth metal compound or an iron, copper or lead compound, with an alcohol, in the liquid phase, in the presence of an expanded bed of an etherification solid catalyst of the sulfonic resin type in acid form, in a circuit of two or more successive reaction zones wherethrough the order of passage of the reactants is periodically modified by disconnecting the first zone from the circuit, feeding the reactants to the second zone, replacing the catalyst of the first zone with fresh catalyst and thereafter connecting said first zone at the end of the circuit.

9 Claims, 1 Drawing Figure

U.S. Patent
Dec. 28, 1982
4,366,327
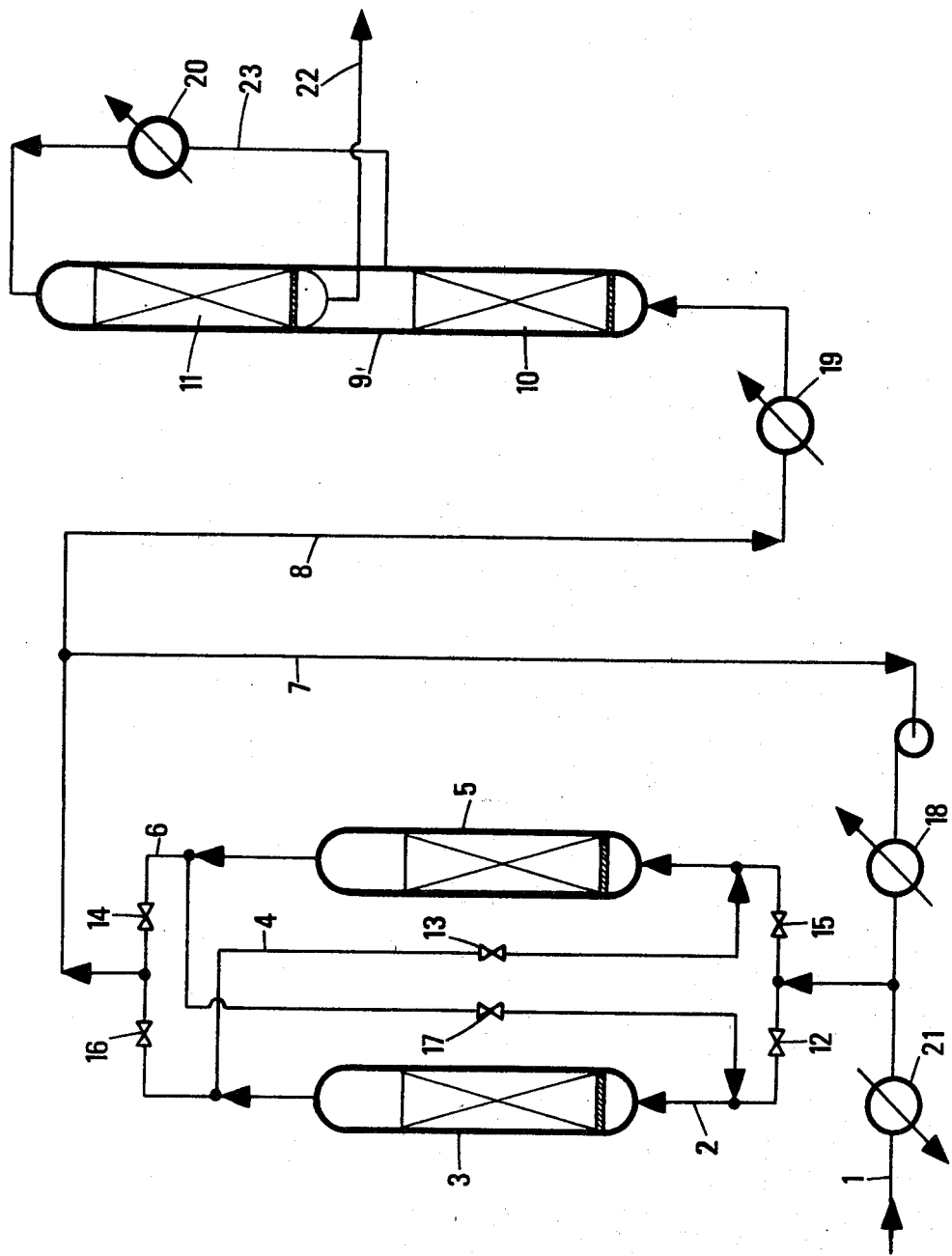

PROCESS FOR PRODUCING ETHERS BY REACTING OLEFINS WITH ALCOHOLS

BACKGROUND OF THE INVENTION

This invention concerns the production of ethers by reacting at least one alcohol with at least one mono-olefin comprising a double bond on a tertiary carbon atom.

It is well known to conduct this reaction in the presence of acid catalysts, and particularly in the presence of solid ion exchange resins in an acid form, the best results being obtained when using macroreticular solid sulfonic resins, e.g. those described in U.S. Pat. No. 3,037,052.

The alcohol is, for example, methanol or ethanol and the mono-olefin is a mono-olefin having a double bond on a tertiary carbon atom, for example isobutene, 2-methyl-1-butene, 2-methyl-2-butene, 2-methyl-1-pentene or 2-methyl-2-pentene. Olefin mixtures may be used; the olefins of the above-mentioned type, for example isobutene, are much more reactive than the bi-secondary olefins such, for example, as 2-butene or the primary-secondary olefins, for example 1-butene, so that it is possible to proceed with mixtures of olefins: the olefins having a tertiary carbon atom are almost the only ones which react, thus providing means for removing said olefins from a hydrocarbon stream, for example a $C_4$ cut produced by steam-cracking or catalytic cracking and which may contain butadiene and/or saturated hydrocarbons.

The reaction of addition of alcohols onto the olefins which leads to the formation of ethers is a balanced and exothermic reaction.

It is therefore necessary on the one hand, to efficiently remove the reaction heat since the sulfonic resins do not withstand for a long time temperatures higher than 120° C. and abrupt heat shocks are detrimental to the mechanical strength of the resin. On the other hand, it is obvious that, in order to achieve high conversion rates, it is preferable to conduct the reaction at low temperature but the efficiency is then limited by the resin activity itself.

Different proposals for conducting this reaction of addition of alcohols onto olefins have been made. It is known, for example, to pass the reactants in the liquid state through a fixed bed of catalyst particles. It has been found that, with regard to the mechanical strength of the resin and in order to avoid too high and irreversible increases of the pressure drop due to the packing of the resin, it is desirable to arrange the catalyst in a certain number of catalyst layers of small height and to cool down the liquid when passing from a catalyst lower to the next one. In another embodiment of fixed bed, the liquid is passed through several parallel tubes containing the catalyst and is cooled externally. However, in this case, the reactor is of a very complex and expensive type and, furthermore, it is difficult to avoid an uneven distribution of the liquid stream in the tubes, which results in a bad operation of the reactor and a quick deterioration of the resin.

The use of a reactor containing a catalyst dispersed in the reactants liquid phase does not provide for high olefin conversion rates unless reactors of excessive volume are used.

It has also been proposed, in order to obtain high conversion rates, to conduct the reaction in two serially arranged reactors with an intermediate separation of the product and to make use of a molar ratio alcohol/olefin higher than 1. In these various cases, however, the energy consumption for the distillation, either of the hydrocarbon cut, for example a $C_4$ cut, or of the methanol or other alcohol in excess which must be recycled, is very substantially increased.

It has also been proposed to proceed to the reaction with two successive catalyst beds (German Federal Republic patent application No. 1934422). In the first bed, the catalyst is maintained in a dispersed state in the liquid by vaporizing one or more of the liquid constituents in order to remove partly the heat produced by the reaction. The second bed consists of the catalyst accumulated at the bottom of the reactor. The temperature conditions are accordingly substantially the same for the first and the second catalyst beds. The liquid circulates downwardly.

It has been found that this method suffers from a major disadvantage: the vapor phase is formed inside or at the contact of the resin particles and forms a layer surrounding them, impeding the free access of the reactants, thereby resulting in relatively poor conversions and selectivities and in a reduced life time of the catalyst. Another disadvantage results from the fact that the compound having the lower boiling point is vaporized and it is, in most cases, the diolefin which thus does not participate in the reaction or at least creates unbalanced conditions as far as the proportions of the reactants are concerned.

The French patent application No. 7831768 proposes to avoid these drawbacks by the following procedure:

A fresh liquid mixture of reactants comprising the alcohol and the olefin, is passed with a liquid recycle stream amounting to from 0.1 to 15 times the liquid rate of the fresh reactants, upwardly through a reaction zone (A) containing particles of solid catalyst of the sulfonated ion exchange resin type, in acid form, at a temperature of 60°–120° C. and selected lower than the boiling temperature of the most volatile constituent of the mixture, under the selected pressure; the feeding rate of this mixture is maintained at a level sufficient for expanding the volume of said bed by at least 2% and to disperse the particles, but insufficient for carrying away the catalyst to a noticeable extent out from said zone (A), the contact time being so selected as to convert 40–95% of said olefin; a first proportion of the liquid mixture resulting from the reaction is withdrawn, cooled down and fed back to the reaction zone (A) as recycle stream and another portion is fed to a second reaction zone (B), containing a solid catalyst in fixed bed of the same type as in zone (A), at a temperature of 30°–70° C., itself selected lower than the boiling temperature of the most volatile constituent, under the selected pressure.

The preferred temperature (zone A) is 75°–100° C. for the $C_4$ hydrocarbons and 65°–90° C. for the $C_5$ hydrocarbons.

The charge in the reaction zone (B) has accordingly the same composition as the effluent from reaction zone (A).

This process may be conducted in adiabatic reactors of a simple design and low cost. The heat produced by a reaction in the first reaction zone may be used partly to heat the reactants charge, the heat excess being optionally removed outside of the reaction zone by passing the effluent through a conventional heat exchanger before its recycling to the inlet of said zone. The stirring of the catalyst in the first reactor avoids the disadvantages relative to the increase of the pressure drop and, as a result of a better homogenization of the temperature suppresses the thermal shocks in the resin. The recirculation of the effluent, which is cooled down in an external exchanger, provides for a better control of the temperature and concentration gradients in the reaction zone and makes possible to operate with the resin at a higher temperature. It is observed that all of these particular operating conditions provide, in spite of the high temperatures in the first reaction zone, higher selectivities in MTBE and a longer life time of the resin.

The process gives satisfactory results in most cases.

It has however been observed that, when the hydrocarbon charge contains certain impurities, the life time of the catalyst is substantially reduced. Among the noxious impurities, there can be mentioned sulfur compounds and particularly the basic organic nitrogen compounds and certain metal ions, particularly those of alkali or alkaline-earth metals or those of iron, copper or lead.

These impurities may be originally present in certain charges or may be produced during preliminary treatments to which the charge has been subjected. For example, it is usual to treat the cracking fractions with inorganic bases, for example sodium hydroxide, or organic bases, for example an alkanolamine. The impurities may also be present in the alcohol, particularly in methanol.

As a general rule, all the compounds capable of reacting with the free sulfonic acid group of the resin may be considered as impurities. The problem arises particularly when the content in these impurities is higher than two parts per million by weight (expressed as NaOH).

It has thus been observed that the decrease in the catalyst activity in the first step makes it necessary to discontinue the operation as soon as this activity falls below a determined value, for example below 50% of the initial activity. Since the partially deactivated catalyst cannot be regenerated economically, it is necessary to discharge it entirely.

The process of the present invention avoids this disadvantage.

SUMMARY OF THE INVENTION

According to the invention, the operation is conducted in at least two separate reaction zones $A_1$ and $A_2$, which are generally arranged in series. These zones are operated with a catalyst bed expanded in the reactants liquid phase. In a first period, all of the reactants pass through the two zones in series in the direction $A_1 \rightarrow A_2$. When the catalyst activity in zone $A_1$ falls below a selected value, for example 30% of the initial activity, zone A is disconnected and the reactants are directly fed to the zone $A_2$; zone $A_1$ may then be emptied and the used catalyst thereof replaced with fresh catalyst. Then, the reactants are passed through the two reactors in the direction $A_2 \rightarrow A_1$. When the activity of the catalyst of $A_2$ becomes too low, the reactants are fed directly to $A_1$, $A_2$ being disconnected. The used catalyst of $A_2$ is replaced with fresh catalyst and then the reactants are fed to $A_1$, then $A_2$. A new cycle may be started again.

It is also possible to proceed with more reaction zones in series, for example 3, 4 or more. Periodically, the first zone is disconnected from the circuit and, after replacement of the catalyst with fresh catalyst, it is reconnected to the circuit in the last position.

BRIEF DESCRIPTION OF THE DRAWING

The FIGURE illustrates the process of the invention schematically.

DETAILED DISCUSSION

The present process is based on the following observation: the deactivation of the catalyst essentially concerns the first catalyst zone wherethrough is passed the reactant charge. A substantial deactivation of the second catalyst zone is only observed when the first catalyst zone has already lost about 80 to 95% of its activity. It thus appears that the first zone has a protecting effect on the second zone.

The recycling which is mentioned in the above French patent is conducted with the effluent of the one or more above-mentioned zones, operated with a catalyst in expanded bed and this effluent is introduced at least in major part at the inlet of said one or more zones. The other portion of the effluent may be fed to a fractionation zone; it is however preferred to supply it to a finishing catalytic zone comprising a fixed bed catalyst, as disclosed in the above-mentioned French patent.

The circulation flow rate of the liquid mixture, in the expanded catalyst reaction zone, depends on the size and the density of the catalyst particles. In most cases, this flow rate is from 0.5 to 10 cm/sec. preferably 1 to 4 cm/sec.

The size of the catalyst particles is, in most cases, from 0.05 to 5 mm, preferably from 0.3 to 1.5 mm when the flow rate is from 1 to 4 cm/sec. The recycle rate is, in most cases, from 0.1 to 15 times, preferably 0.5 to 4 times the flow rate of the reactants fresh charge. The latter is usually from 0.5 to 20 liquid volumes of the reactor containing the catalyst and per hour (hourly space velocity).

A more detailed description of the catalyst is given, for example, in U.S. Pat. No. 3,037,052.

The pressure must be sufficient to maintain the reactants in the liquid phase at a temperature above the boiling point of the most volatile constituent of the charge. Except for this provision, the pressure is usually from 5 to 50 bars.

The conversion of the reactive olefin is selected from 60 to 95%, preferably from 75 to 92%, in the first reaction zone, in the case of isobutene and from 40 to 75%, preferably from 50 to 70%, in the case of 2-methyl 1-and 2-butenes.

In the reaction zone with a fixed bed catalyst, when used to complete the reaction, the catalyst may be selected with a particle size such as defined for the first reaction zone. The conversion of the reactive olefin is preferably so selected that the total conversion is at least 90%, of which at least 3% in the fixed bed reaction zone, in the case of isobutene, and at least 70%, of which at least 3% in the fixed bed reaction zone, in the case of 2-methyl 1-and 2-butenes.

The invention is illustrated by the accompanying drawing.

The mixture of the reactants, alcohol and isobutene or olefinic $C_4$ cut, is fed through lines 1 and 2 to reactor 3 containing a dispersed catalyst. It is discharged through line 4 and fed to reactor 5 containing a dispersed catalyst. The product is discharged through line 6, a portion thereof is recycled through line 7 and another portion is fed through line 8 either directly to the fractionation stage or to a fixed bed reactor, which optionally may consist of two separate beds 10 and 11 communicating through line 23. The valves 12, 13, 14 are open and the valves 15, 16, 17 are closed during this operation. The products are discharged through line 22.

When the activity of the catalyst in reactor 3 becomes too low, the valves 12 and 13 are closed and valve 15 is opened; the used catalyst of reactor 3 is replaced with fresh catalyst and the reactors are then serially connected by closing the valve 14 and opening the valves 17 and 16. Thus, the charge passes successively through reactor 5 and reactor 3.

When the activity of the catalyst in reactor 5 becomes too low, the valves 15 and 17 are closed and the valve 12 is opened. As soon as the catalyst of reactor 5 has been replaced, the valve 16 is closed and the valves 13 and 14 are opened. The charge thus passes through reactor 3 and then through reactor 5.

Coolers have been indicated by reference numerals 18, 19 and 20; they are not absolutely necessary. Similarly, the heater 21 may be necessary at the beginning of an operation but it is no longer necessary thereafter, the recycle stream providing for a part or the totality of the heat required for heating the fresh charge.

Another procedure consists of making use exclusively of reaction zones operated with a catalyst expanded in the liquid phase of the reactants without passing the effluents through the fixed bed reaction zones. In this case, it may be appropriate to cool down the effluent between the successive reaction zones and to proceed to the recycling of a portion of the effluent from one given zone to the inlet of the same zone.

In the following examples, the temperature is maintained below the boiling temperature. Example 1 is given by way of comparison, examples 2 and 3 illustrate the invention.

EXAMPLE 1

A $C_4$ cut, consisting of a mixture of a steam cracking cut with a catalytic cracking cut, used as olefin containing charge, has the following composition:
- propane: 1.0% by weight
- isobutane: 22.2% by weight
- isobutene: 29.4% by weight
- n-butane: 11.4% by weight
- n-butenes: 35.5% by weight
- pentane: 0.5% by weight
- alkalinity: 10 ppm (expressed as NaOH)

This charge is admixed with methanol to provide a methanol/isobutene molar ratio of 1.18 and the whole mixture is introduced in the liquid state at the bottom of a first reactor arranged vertically and containing 0.5 m³ of Amberlyst 15 sulfonic resin (particle size: 0.4 to 1 mm). To the reactants mixture, there is added a portion of the effluent from said first reactor, so that the linear velocity of the whole stream amounts to 2 cm/sec. Under these conditions, the catalyst bed is subjected to a 25% expansion. The recycled effluent, whose temperature is 90° C. at the beginning of the cycle, is also used to heat a portion of the charge to a temperature of 70° C. at the inlet of the reactor. The reaction is conducted in the liquid phase while maintaining the pressure in the reactor to 20 atmospheres. The fresh charge ($C_4$ cut + methanol) is introduced at a rate of 2.2 tons per hour. The effluent is then cooled down to 58° C. and introduced into the second reactor, containing 1.3 m³ of Amberlyst 15 resin arranged in fixed bed, where the reaction is conducted under adiabatic conditions.

The results are given in Table 1 below. It is observed that, after 1200 to 1500 hours of run, the conversion rate of isobutene at the outlet of the first reactor begins to decrease substantially and, accordingly, it is not possible to obtain the desired total conversion rate of isobutene.

TABLE 1

| Time in hours | 20 | 600 | 1200 | 1500 | 1800 | 2400 |
|---|---|---|---|---|---|---|
| First reactor outlet isobutene conversion % | 83 | 82 | 80 | 70 | 55 | 10 |
| Second reactor outlet $1^{st}$ + $2^{nd}$ reactors isobutene conversion % | 96 | 96 | 96 | 90 | 80* | 50* |

*Substantial formation of dimers

It is thus necessary, after 1200 to 1500 hours, to completely stop the unit and discharge the 500 liters of partially poisoned catalyst and to replace them with fresh catalyst.

EXAMPLE 2

This example illustrates the process of the present invention.

A $C_4$ cut having the same composition as in example 1 is admixed with methanol to provide a methanol/isobutene molar ratio of 1.18 and the whole mixture is fed at the rate of 2.2 tons per hour, in the liquid state, to a reactor assembly shown in the accompanying drawing.

The mixture of reactants is introduced through lines 1 and 2 at the bottom of the first reactor (3) arranged vertically and containing 0.25 m³ of Amberlyst 15 resin (grain size: 0.4 to 1 mm). It is discharged through line (4) to be fed to the bottom of a second reactor (5) also arranged vertically and containing 0.25 m³ of the same resin. The product is discharged through line (6). A portion of said product, whose temperature is 90° C., is recycled through line (7) to the bottom of reactor (3) at such a recycled rate that the linear velocity of the whole mixture is 2 cm/sec.

The temperature at the inlet of reactor (3) is adjusted to 70° C. by means of the heater 21 and by using the heat obtained by the recycling. The reaction is conducted in liquid phase by maintaining the pressure at 20 atmospheres. The effluent is then cooled down to 58° C. and introduced into a third reactor (9) containing 1.3 m³ of Amberlyst 15 resin arranged in fixed bed, where the reaction proceeds under adiabatic conditions. During the first phase of the operation, the valves 15, 16, 17 are closed.

After 1500 hours of run, the valves 12 and 13 are closed and the valve 15 is opened. Without discontinuing the operation, the used catalyst of reactor (3) is replaced with fresh catalyst, this operation being performed in about 10 hours. Then, the reactors are again serially connected by closing the valve 14 and by opening the valves 17 and 16. After 3000 hours of run, the catalyst of reactor (5) is replaced, and so on.

Every 1500 hours, there is thus replaced 0.25 m³ of catalyst. The results are given in Table II

TABLE II

| Time hours | 20 | 600 | 1200 | 1500 | 1800 | 2400 | 3000 |
|---|---|---|---|---|---|---|---|
| Effluent from line 8 isobutene conversion % | 83 | 82 | 81 | 80 | 82.5 | 81.5 | 80 |
| Effluent from line 22 isobutene conversion % | | | | | | | |

TABLE II-continued

| Time hours | 20 | 600 | 1200 | 1500 | 1800 | 2400 | 3000 |
|---|---|---|---|---|---|---|---|
| 1$^{st}$ and 2$^{nd}$ reactors | 96 | 96 | 96 | 96 | 96 | 96 | 96 |

Thus, by making use of 0.5 m³ of resin in the two serially connected reaction zones rather than in a single one, it is observed that the amount of wasted used catalyst is 0.5 m³ every 3000 hours instead of 0.5 m³ every 1500 hours, in the other case. Moreover, it is unnecessary to discontinue the operation of the unit and the operating cycle may be as long as several tens of thousand hours, whereas in the case of example 1, the unit must be stopped every 1500 hours.

EXAMPLE 3

This example illustrates the possibility of synthesizing ethers by making use of only two serially arranged reactors with expanded beds and without fixed bed reactor. There is used a steam cracking C$_5$ cut having the following composition:

| | |
|---|---|
| C$_3$—C$_4$ hydrocarbons | 1.8% by weight |
| C$_5$ saturated hydrocarbons | 31.6% " |
| 2-methyl 1-butene | 5.4% " |
| 2-methyl 2-butene | 27.2% " |
| Other C$_5$ olefins | 34.0% " |
| Alkalinity | 20 ppm (expressed as NaOH) |

This cut is admixed with methanol to provide a molar ratio of methanol to 2-methyl-1-butene +2 methyl-2-butene of 1.3 and the whole mixture is introduced at a rate of 0.6 m³ per hour at the bottom of a first reactor A arranged vertically and containing 0.2 m³ of Amberlyst 15 resin. A portion of the effluent from said reactor is recycled to the inlet of the first reactor at a recycle rate such that the linear velocity of the whole mixture be equal to 1.5 cm/sec. The temperature at the inlet of this first reactor is adjusted at 70° C. The other portion of the effluent is cooled to 52° C. and fed to the bottom of a second reactor B arranged vertically and also containing 0.2 m³ of the same resin. A portion of the effluent from said second reactor is recycled to the inlet of said second reactor with a recycling rate such that the linear velocity be also of 1.5 cm/sec. The expansion rate of the catalyst beds in both cases is 20%. As the first catalyst bed becomes poisoned, the temperature at the inlet of the second reactor is progressively increased, as indicated in the following table. The results are given in Table III.

TABLE III

| Time in hours | 20 | 600 | 1500 | 2300 | 3000 |
|---|---|---|---|---|---|
| 1$^{st}$ reactor | | | | | |
| Isoamylene conversion % | 69.0 | 68.0 | 67.0 | 42.0 | 5.0 |
| 2$^{nd}$ reactor | | | | | |
| Temperature at inlet | 52 | 55 | 58 | 60 | 65 |
| Isoamylene conversion % (1$^{st}$ and 2$^{nd}$ reactors) | 74.0 | 74.0 | 73.6 | 70.5 | 68.2 |

After 3000 hours, the first reactor is almost completely poisoned. The 200 liters of catalyst present therein are then replaced, without stopping the unit, and the charge is fed at 70° C. to reactor B which becomes the first one. When the resin has been charged again in reactor A, the latter is placed in second position with a temperature programm during time as indicated in the table.

There is thus discharged as waste 0.2 m³ of catalyst every 3000 hours without stopping the unit.

By way of comparison, when making use of 0.4 m³ of catalyst in a single reactor of the same type, the conversion of the isoamylenes falls to 68% after 1500 hours and the unit must be stopped to discharge these 0.4 m³ of resin.

In the above examples, the content of impurities was expressed by the "alkalinity" calculated as NaOH. The statement of an impurity content x of a hydrocarbon cut means that said cut had the same neutralization power with respect to free acid groups of the sulfonic resin as that observed with an equal volume of an impurity-free cut having a NaOH content of x.

In practice, the determination may be made by passing a sufficient known volume of hydrocarbon cut through a sulfonic acid resin bed of known acidity and by then determining the residual acidity of the resin with sodium hydroxide.

What is claimed is:

1. In a process for producing an ether by reacting an olefin with an alcohol in the liquid phase, in the presence of a solid etherification catalyst of the sulfonic resin type in acid form, in expanded bed, the improvement comprising effecting the reaction in at least two reaction zones in series, periodically modifying the order of passage of the reactants through the reaction zones by disconnecting from the circuit the first zone through which the charge passes and feeding the reactants directly to the following reaction zone, replacing the used catalyst of the disconnected zone with fresh catalyst, and connecting the resultant zone containing fresh catalyst to the circuit in the last position.

2. A process according to claim 1, wherein the reaction product is fed to a finishing reaction zone containing a solid etherification catalyst of the acid type in fixed bed.

3. A process according to claim 1, wherein the reactants charge contains at least 2 ppm by weight of impurities, expressed as NaOH.

4. A process according to claim 1, wherein the olefin is used as a catalytic cracking C$_4$ olefinic cut containing at least one alkanolamine as impurity.

5. A process according to claim 1, wherein the olefin is used as a catalytic cracking C$_4$ olefinic cut containing sodium hydroxide as impurity.

6. A process according to claim 1, wherein the olefin is used as a catalytic cracking C$_4$ olefinic cut containing at least one compound of alkaline-earth metal, iron, copper or lead as impurity.

7. A process according to claim 1, wherein the temperature of each of the reaction zones is progressively increased during time, so as to maintain a substantially constant conversion rate in each of said zones.

8. A process according to claim 1, wherein a portion of the effluent of at least one of the reaction zones is recirculated through the same zone.

9. A process according to claim 1, wherein a portion of the effluent of the last reaction zone is fed to the inlet of the first reaction zone.

* * * * *